United States Patent [19]

Young et al.

[11] Patent Number: 4,950,379

[45] Date of Patent: Aug. 21, 1990

[54] POLAROGRAPHIC CELL

[75] Inventors: Chung C. Young, Weston; James E. Fowler, Watertown; Alan R. Silverman, Hyde Park, all of Mass.

[73] Assignee: Nova Biomedical Corporation, Waltham, Mass.

[21] Appl. No.: 418,775

[22] Filed: Oct. 2, 1989

Related U.S. Application Data

[63] Continuation of Ser. No. 155,196, Feb. 12, 1988, abandoned, which is a continuation-in-part of Ser. No. 36,495, Apr. 9, 1987, Pat. No. 4,759,828, which is a continuation-in-part of Ser. No. 152,836, Feb. 5, 1988, abandoned.

[51] Int. Cl.$^5$ .............................................. G01N 27/31
[52] U.S. Cl. .................................... 204/403; 204/415; 204/435; 435/817
[58] Field of Search ............... 204/435, 1 E, 403, 415; 435/817

[56] References Cited

U.S. PATENT DOCUMENTS

| | | | |
|---|---|---|---|
| 3,098,813 | 7/1963 | Beebe et al. | 204/195 |
| 3,539,455 | 11/1970 | Clark | 204/1 |
| 3,542,662 | 11/1970 | Hicks et al. | 204/195 |
| 3,575,836 | 4/1971 | Sternberg | 204/195 |
| 3,707,455 | 12/1972 | Derr et al. | 204/195 |
| 3,718,563 | 2/1973 | Krull et al. | 204/195 |
| 3,776,819 | 12/1973 | Williams | 204/1 T |
| 3,838,033 | 9/1974 | Mindt et al. | 204/195 |
| 3,869,354 | 3/1975 | Montalvo, Jr. | 204/1 |
| 3,957,613 | 5/1976 | Macur | 204/412 |
| 3,979,274 | 9/1976 | Newman | 204/195 |
| 4,073,713 | 2/1978 | Newman | 204/195 |
| 4,220,503 | 9/1980 | Johnson | 204/1 |
| 4,356,074 | 10/1982 | Johnson | 204/195 |
| 4,388,166 | 6/1983 | Suzuki et al. | 204/403 |
| 4,404,066 | 9/1983 | Johnson | 204/1 |

FOREIGN PATENT DOCUMENTS 603671  8/1960  Canada ............................ 204/435

OTHER PUBLICATIONS

Wingard Jr., et al., *J. of Biomedical Materials*, "Immobilized Enzyme Electrodes for the Potentiometric Measurement of Glucose Concentration: Immobilization Techniques and Materials", vol. 13, (1979), pp. 921–935.

Iriyama et al., *Jikeikai Medical Journal*, "A Convenient Method for Preparing A Glucose Sensor", vol. 29, (1982), pp. 889–346.

Clark et al., *Annals of the N.Y. Acad. of Sci.*, "Electrode Systems for Continuous Monitoring in Cardiovascular Surgery", vol. 102, pp. 29–45, (10/31/62).

Gough et al., Anal. Chem., "Two-Dimensional Enzyme Electrode Sensor for Glucose", 57:2351–2357, (10/85).

*Primary Examiner*—G. L. Kaplan

[57] ABSTRACT

A two electrode assembly in a polarographic cell includes a sensor electrode and a silver/silver chloride reference electrode in which silver metal is in contact with a substantial reservoir of silver chloride.

10 Claims, 1 Drawing Sheet

POLAROGRAPHIC CELL

This is a continuation of Ser. No. 07/155,196 filed on Feb. 12, 1988 and now abandoned which in turn was a continuation-in-part of 07/152,836 filed on Feb. 5, 1988 and now abandoned which in turn was a continuation-in-part of 07/036,495 filed on Apr. 9, 1987 and now U.S. Pat. No. 4,759,828.

BACKGROUND OF THE INVENTION

This invention relates to polarographic cells including a silver/silver chloride reference electrode.

In polarographic cells having two electrodes, one electrode is polarized in the presence of the substance being measured and is known as the sensor electrode. The second electrode is depolarized in the presence of the substance being measured and is known as the reference electrode. An electrolyte generally provides an electrical path between the two electrodes, which otherwise are in an electrically insulating relation. In the presence of the substance being measured a current passes between the electrodes, the current being, at a given applied voltage, proportional to the concentration of the substance. The voltage applied to the cell is the potential of the sensor relative to that of the reference electrode; the potential of the reference electrode should therefore be constant. The current passing between the electrodes may result in undersirable potential changes at the reference electrode. To counter this effect a third, counter, electrode is often used so that the current generated will pass between the sensor and counter electrode.

SUMMARY OF THE INVENTION

In general, the invention features a two electrode assembly for use in a polarographic cell. One electrode in the assembly is a standard sensor electrode. The second electrode is a silver/silver chloride reference electrode in which silver metal is in contact with a reservoir of silver chloride. During the operation of the assembly a current passes between the two electrodes and causes silver ion to be reduced to silver metal. The silver chloride reservoir supplies sufficient silver ion so that the effect of the consumption of the silver ion on the potential of the reference electrode is minimal, thereby avoiding the necessity of using a counter electrode.

By reservoir, it is meant that enough silver chloride is present so that the assembly can be used for at least 1,000 assays, preferably 2,000 or more, without using up the supply; more than just a thin (less than $10\mu$) layer of silver chloride must be present.

In a preferred embodiment, the reference electrode is a silver ring surrounded (at any position on the ring) by a concentric ring of silver chloride that is at least $25\mu$ thick, more preferably at least 0.01 cm thick; and the sensor electrode (e.g., a standard platinum electrode) is disposed inside the concentric rings.

A preferred use of this assembly is in enzyme electrodes in which a laminated membrane covers the solution-contacting face of the sensor and reference electrodes. The laminated membrane generally includes an inner membrane adjacent the solution-contacting face; an outer solution-contacting membrane; and an adhesive enzyme layer between the membranes holding them together. The substance being assayed (e.g., glucose) is oxidized by the enzyme to generate a second substance, e.g., $H_2O_2$, to which the sensor electrode is sensitive. A preferred construction of the laminated membrane is described in Young et al., U.S. Ser. No. 152,836, filed Feb. 5, 1988, of which the present application is a continuation in-part and which is hereby incorporated by reference herein.

The electrode assembly is easy to construct, easy to handle, and can be used for many assays without needing to replenish the supply of silver chloride. Advantageously, only two electrodes need be used in the cell.

Other features and advantages of the invention will be apparent from the following description of the preferred embodiments thereof and from the claims.

DESCRIPTION OF THE PREFERRED EMBODIMENT

Figure 1:
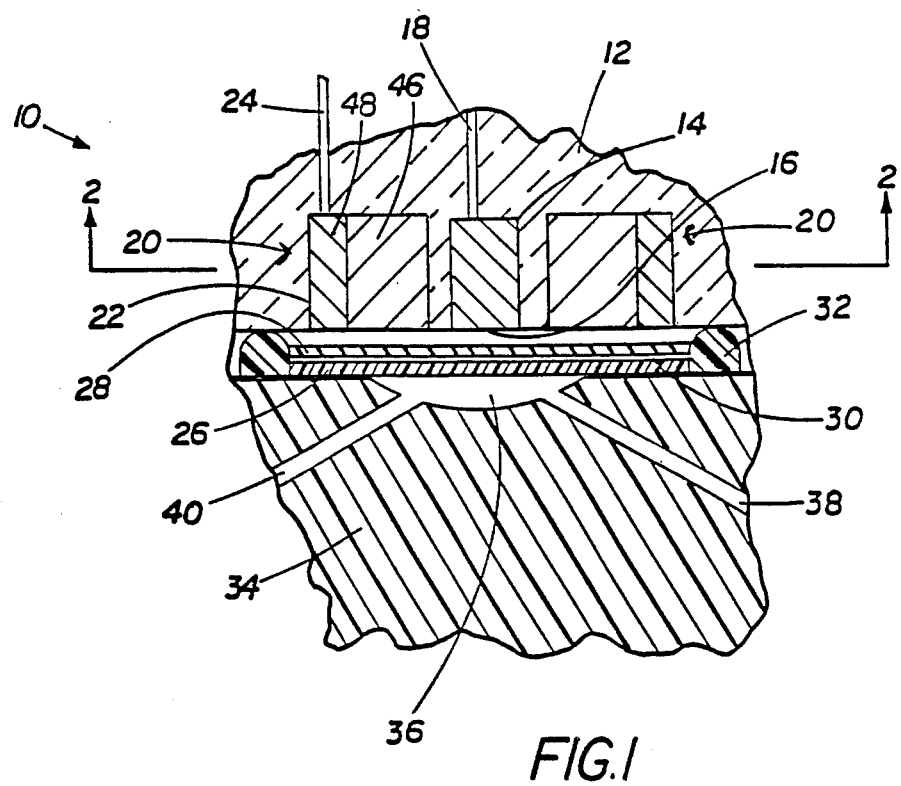
FIG. 1 is a view in section, partially broken away, showing an embodiment of the present invention including a flow chamber, on an enlarged scale.

Referring to the FIG. 1, a glucose electrode 10 comprises an electrically insulating support body 12 which may be of elongated cylindrical shape carrying at its end a platinum sensor electrode or anode 14 having an active or exposed face 16 and a conductor 18. The lower end of the support body 12 also carries a silver/silver chloride reference electrode 20 having an exposed face 22 and a conductor 24. Conductors 18 and 4 lead to an amperometer (not shown). Disposed across the exposed faces of the electrodes is a laminated membrane including an outer membrane 26 and an inner membrane 28 adhesively secured together by an intermediate layer 30 comprising the enzyme glucose oxidase, preferably a mixture of the enzyme and a crosslinking or binding agent such as glutaraldehyde. The laminated membrane is sealed in liquid-tight relation to the lower face of support body 12 by O-ring 32 or any other suitable means.

The outer membrane 26, inner membrane 28, and intermediate layer 30, and a procedure for constructing the laminated membrane, are described in depth in Young et al., supra.

In the embodiment shown in FIG. 1, a flow cell 34 is mounted in liquid-tight relation against the lower face of outer membrane 26, being sealed thereto by a silicone washer or by O-ring 32. Cell 34 may be constructed of polystyrene, polymethacrylate, or any other suitable rigid liquid impervious material and includes a chamber 36 exposed to the face of outer membrane 26 as well as inlet 38 and outlet 40. In a preferred embodiment, the volume of chamber 36 together with inlet 38 and outlet 40 is approximately 5 to 10 microliters.

Figure 2:
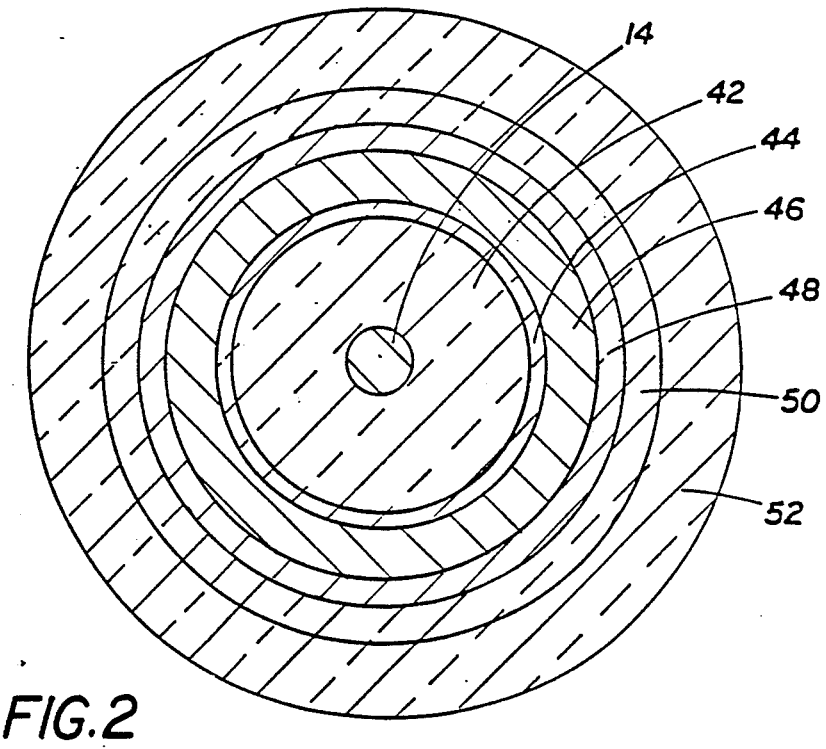
FIG. 2 is a view in section at 2—2 of FIG. 1.

Referring to FIG. 2, the support body 12 has 0.016 inch diameter central platinum sensor electrode 14 surrounded by concentric rings including one of lead glass (42) (Corning 0120 type; 0.095 inch O.D.); versilok structural adhesive (44) (0.005 inch thick); silver (46) (0.105 inch I.D.; 0.125 inch O.D.); a 60–40 mixture of silver sulfide ($Ag_2S$)-silver chloride (AgCl) (48) (0.01 inch thick); potting material epoxy (50) (0.02 inch thick); and Noryl (52) (0.337 inch O.D.). Rings 46 and 48 are the silver/silver chloride reference electrode 20, and are about 0.75 cm in height. The AgCl ring 48 is the same height as the silver metal ring and provides an adequate supply of silver ion so that the changes in potential at the reference electrode caused by the current is minimal. A reference electrode having an 0.01 inch thick ring can be used for thousands of measurements; a counter electrode is not needed with the assembly. In general, the AgCl ring should be at least 25μ, more preferably at least 0.01 cm thick, to provide the adequate supply of silver ion; there is no real upper limit on thickness, although as a practical matter the ring probably should not be thicker than about 0.5 cm. $Ag_2S$ is mixed with the AgCl to make the ring easier to work with.

The amount of silver chloride needed in the reservoir (in any assembly) to provide sufficient $Ag^+$ for 2,000 assays depends on the amount of current in a typical assay, and the length of the typical assay. One skilled in the art will know how to readily obtain these values. For the preferred assembly, the typical current is about 5 nanoamps, and the length of a typical assay is 60 sec. This converts to $3 \cdot 10^{-7}$ coulombs per assay. The minimum amount of AgCl that should be in the reservoir is readily obtained by dividing the number of coulombs for 2,000 assays by 96,400 coulombs/mole, and then multiplying the value obtained by the molecular weight of AgCl.

In a typical assay, a body fluid, e.g., whole blood, is flowed through the inlet 38 and fills the sample chamber 36. When the outer membrane 26 contacts the whole blood, glucose molecules and oxygen molecules present in the sample pas through it and contact the enzyme in layer 30; the enzyme catalyzes the oxidation of glucose to gluconic acid. The hydrogen peroxide produced during the oxidation passes through membrane 28 and contacts surface 16 of sensor electrode 14, which is poised at +700 mV in relation to reference electrode 20, and also contacts the face 22 of reference electrode 20, forming an electroconductive path between the two electrodes. A current is generated, the magnitude rising to a constant (steady state) value (response) related to the equilibrium concentration of the hydrogen peroxide. The current causes the consumption of $Ag^+$ (from AgCl) in the reference electrode; because of the reservoir of AgCl, however, the effect of this consumption on the potential of the reference electrode is minimized for thousands of assays.

OTHER EMBODIMENTS

Other embodiments are within the following claims. For example, the preferred electrode can be designed to assay other substances besides glucose, provided the enzyme in the layer 30 oxidizes the substance to generate hydrogen peroxide, as desired in Young et al., supra.

One skilled in the art will recognize that the AgCl reservoir in contact with the silver metal can be one-half or one-quarter the height of the silver ring, or can be a half-ring, quarter-ring, etc., so long as sufficient AgCl is present to avoid changes in potential. For example, a half-ring of AgCl (one-half of a concentric ring) of the same thickness as ring 48 can be used. Moreover, the silver metal can be non-ring shapes, provided that in whatever configuration is selected the metal is in contact with a AgCl reservoir. Furthermore, two electrode assemblies in accordance with the invention can, of course, be used in other types of polarographic cells, aside from enzyme electrodes having a laminated membrane.

We claim:

1. A polarographic cell comprising a sensor electrode and a reference electrode,
    said reference electrode being a silver/silver chloride electrode comprising a ring of silver metal in contact with a concentric ring of silver chloride that has a thickness of at least 25μ, said reference electrode being capable of serving as a counter electrode to complete an electric circuit with said sensor electrode, a sufficient quantity of silver chloride being present so that 2,000 assays can be performed where the current used in each assay is 5 nanoamps and the length of each assay is 60 seconds.
    wherein during the operation of said electrode assembly, current flows through said electric circuit and the silver ion from said silver chloride is reduced to silver metal, said cell being connected to means for measuring said current, and
    wherein said polarographic cell lacks a third electrode.

2. The electrode assembly of claim 1 wherein said ring of silver chloride is at least 0.01 cm thick.

3. The electrode assembly of claim 1 wherein said ring of silver chloride is less than 0.5 cm thick.

4. The electrode assembly of claim 1, 2, or 3 wherein said silver chloride ring extends for the entire height of said silver ring.

5. The electrode assembly of claim 1 wherein said sensor electrode is disposed inside of said ring of silver chloride and said ring of silver metal.

6. The electrode assembly of claim 5, further comprising a laminated membrane covering the exposed faces of said sensor and said reference electrodes.

7. The electrode assembly of claim 6 wherein said laminated membrane comprises an inner membrane adjacent said exposed faces of said sensor and said reference electrodes; an outer solution-contacting membrane; and an adhesive layer between said membranes holding them together.

8. The electrode assembly of claim 7 wherein said adhesive layer comprises an enzyme and a binding agent.

9. The electrode assembly of claim 8 wherein said assembly is for use in assaying a substance and wherein said enzyme is capable of oxidizing said substance to generate hydrogen peroxide.

10. The electrode assembly of claim 1, further comprising a laminated membrane covering the exposed faces of said sensor electrode.

* * * * *